United States Patent
Lehmann et al.

(10) Patent No.: US 9,763,694 B2
(45) Date of Patent: Sep. 19, 2017

(54) TELESCOPIC STRUT FOR AN EXTERNAL FIXATOR

(71) Applicant: Stryker European Holdings I, LLC, Kalamazoo, MI (US)

(72) Inventors: Philippe Lehmann, Lamboing (CH); Joël Bouquet, Solothurn (CH)

(73) Assignee: Stryker European Holdings I, LLC, Kalamazoo, MI (US)

( * ) Notice: Subject to any disclaimer, the term of this patent is extended or adjusted under 35 U.S.C. 154(b) by 268 days.

(21) Appl. No.: 14/549,949

(22) Filed: Nov. 21, 2014

(65) Prior Publication Data

US 2015/0080892 A1   Mar. 19, 2015

Related U.S. Application Data

(63) Continuation of application No. 13/589,624, filed on Aug. 20, 2012, now Pat. No. 8,906,021.

(51) Int. Cl.
| | | |
|---|---|---|
| *A61B 17/00* | (2006.01) | |
| *A61B 17/66* | (2006.01) | |
| *A61B 17/62* | (2006.01) | |

(52) U.S. Cl.
CPC .............. *A61B 17/66* (2013.01); *A61B 17/62* (2013.01)

(58) Field of Classification Search
CPC ......... A61B 17/60; A61B 17/62; A61B 17/64; A61B 17/66; A61B 17/6408–17/666
See application file for complete search history.

(56) References Cited

U.S. PATENT DOCUMENTS

| | | |
|---|---|---|
| 1,643,855 A | 9/1927 | Peterson |
| 2,773,529 A | 12/1956 | Valenti |
| 3,855,884 A | 12/1974 | McPeak |
| (Continued) | | |

FOREIGN PATENT DOCUMENTS

| | | |
|---|---|---|
| EP | 0377744 A1 | 7/1990 |
| EP | 2250968 A1 | 11/2010 |
| (Continued) | | |

OTHER PUBLICATIONS

Extended European Search Report for EP10194945.1 dated Feb. 25, 2011.

*Primary Examiner* — Jacqueline Johanas
*Assistant Examiner* — Tessa Matthews
(74) *Attorney, Agent, or Firm* — Lerner, David, Littenberg, Krumholz & Mentlik, LLP

(57) ABSTRACT

A telescopic strut for use with an external fixator comprising an axially extending rod; an axially extending tube moveably recurring the rod for varying the length of the rod and tube combination along a longitudinal axis; the tube having first and second ends, the second end having a pin extending therethrough; a locking system mounted on the tube first end for adjusting the position of the rod in the tube and fixing the length of the rod and tube combination; a coupling element having a tubular sleeve with a threaded outer surface mounted on an outer surface of the second end of the tube, the sleeve having two diametrically opposed slots receiving the pin and an adjustment element threadably mounted on the sleeve outer surface for axial movement along the axis, the adjustment element having a surface contacting the pin to limit the movement of the pin in the slots.

19 Claims, 7 Drawing Sheets

(56) References Cited

U.S. PATENT DOCUMENTS

| | | | |
|---|---|---|---|
| 4,271,731 A | 6/1981 | Suligoy et al. | |
| 4,308,863 A * | 1/1982 | Fischer | A61B 17/62 |
| | | | 606/56 |
| 4,615,338 A | 10/1986 | Ilizarov et al. | |
| 5,207,676 A | 5/1993 | Canadell et al. | |
| 5,702,389 A | 12/1997 | Taylor et al. | |
| 5,823,292 A | 10/1998 | Krause | |
| 5,863,292 A | 1/1999 | Tosic | |
| 5,928,230 A | 7/1999 | Tosic | |
| 6,030,386 A | 2/2000 | Taylor et al. | |
| 6,036,691 A | 3/2000 | Richardson | |
| 6,221,072 B1 | 4/2001 | Termaten | |
| 6,347,564 B1 | 2/2002 | Ciocca | |
| 6,386,074 B1 | 5/2002 | Yang | |
| 6,397,707 B1 * | 6/2002 | Tatarinov | B25B 23/0021 |
| | | | 81/124.1 |
| 6,500,177 B1 | 12/2002 | Martinelli et al. | |
| 7,422,593 B2 | 9/2008 | Cresina et al. | |
| 7,654,175 B2 * | 2/2010 | Hamon | B25B 13/102 |
| | | | 81/125 |
| 8,057,474 B2 | 11/2011 | Knuchel et al. | |
| 8,062,293 B2 | 11/2011 | Steiner et al. | |
| 8,695,461 B2 * | 4/2014 | Moss | B25B 13/06 |
| | | | 81/125 |
| 2002/0037193 A1 | 3/2002 | Gibbons et al. | |
| 2005/0216032 A1 | 9/2005 | Hayden | |
| 2007/0055233 A1 | 3/2007 | Brinker | |
| 2007/0161983 A1 * | 7/2007 | Cresina | A61B 17/66 |
| | | | 606/54 |
| 2008/0195101 A1 | 8/2008 | Lechot et al. | |
| 2009/0198234 A1 | 8/2009 | Knuchel et al. | |
| 2009/0198235 A1 | 8/2009 | Steiner et al. | |
| 2010/0031784 A1 | 2/2010 | Situ | |
| 2011/0082458 A1 | 4/2011 | Crozet et al. | |
| 2011/0208187 A1 | 8/2011 | Wong et al. | |
| 2014/0276817 A1 * | 9/2014 | Murray | A61B 17/62 |
| | | | 606/56 |
| 2014/0276821 A1 * | 9/2014 | Murray | A61B 17/62 |
| | | | 606/57 |
| 2014/0276822 A1 * | 9/2014 | Cresina | A61B 17/6416 |
| | | | 606/57 |
| 2016/0022314 A1 * | 1/2016 | Bordeaux | A61B 17/62 |
| | | | 606/56 |

FOREIGN PATENT DOCUMENTS

| | | |
|---|---|---|
| FR | 2787697 A1 | 6/2000 |
| WO | 2007001945 A1 | 1/2007 |

* cited by examiner

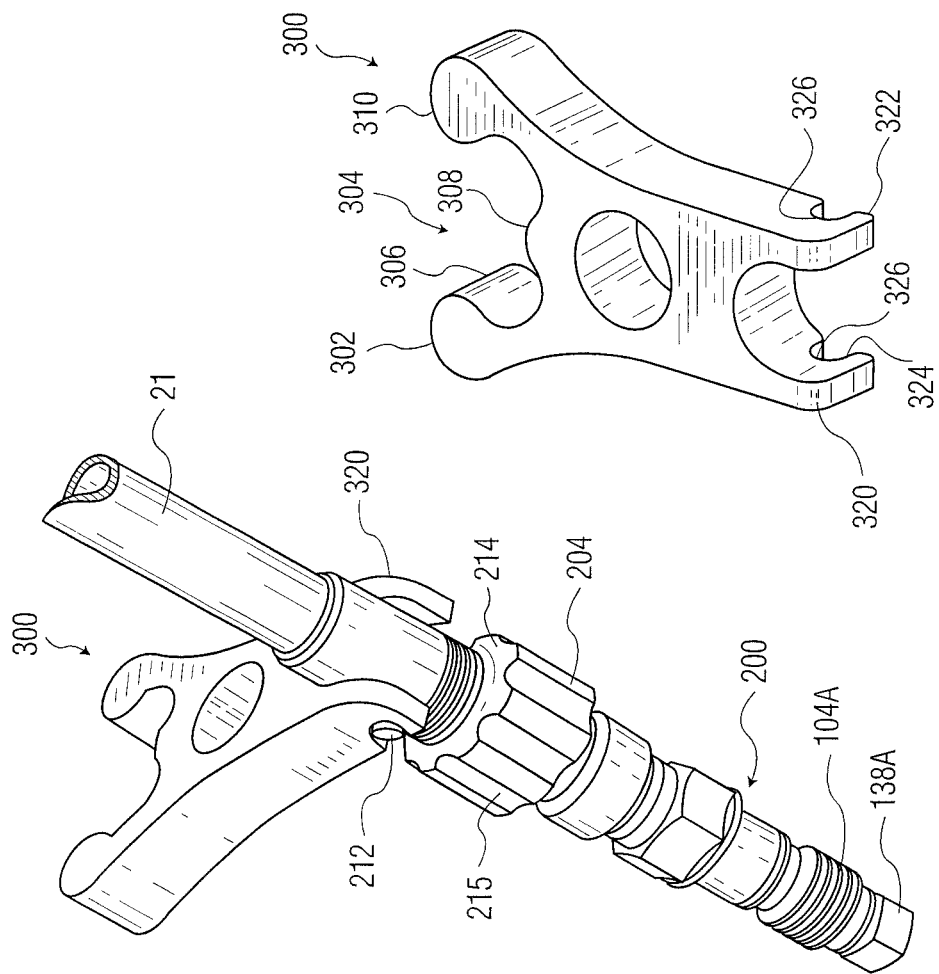
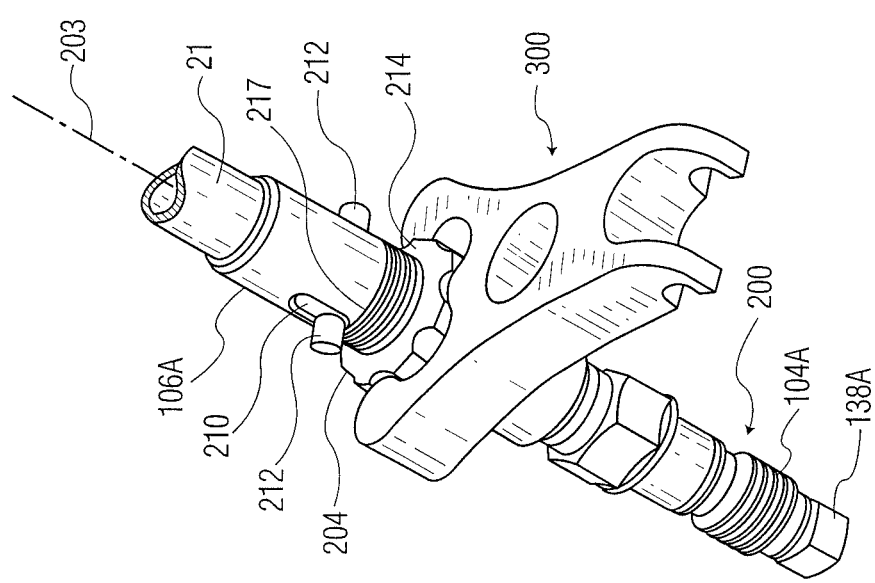
FIG. 9
FIG. 10
FIG. 11

TELESCOPIC STRUT FOR AN EXTERNAL FIXATOR

CROSS-REFERENCE TO RELATED APPLICATIONS

This application is a continuation of U.S. application Ser. No. 13/589,624 filed Aug. 20, 2012, the disclosure of which is incorporated herein by reference.

BACKGROUND OF THE INVENTION

The invention relates to a telescopic strut for an external fixator, especially for use with an external ring fixator.

A plurality of compression-distraction apparatus have been designed and improved by Ilizarov and his group using two external rings to be placed around the limb to be fixed. There are usually at least two such rings, one proximal and one distal ring, which are connected with a plurality of struts or rods. Preferably, these struts are linked to the rings in a way that the attachment points can be pivoted and the length of the strut can be varied to enable adjustment of the external fixation rings.

Ilizarov has also provided some improvements for said systems. European Patent No. 0 377 744 shows a telescopic strut for such an external fixator. U.S. Pat. No. 4,615,338 shows a further device to control the length of such telescopic struts.

A different external ring fixator having telescopic struts is shown in U.S. Pat. Nos. 5,702,389 and 6,030,386. Other telescopic struts are shown in U.S. Pat. Nos. 8,057,474 and 8,062,293 assigned to the assignee of the present invention, the disclosures of which are incorporated herein by reference.

BRIEF SUMMARY OF THE INVENTION

However, these devices, which can be used to shorten or lengthen the telescopic struts, are difficult to adjust and it is one aspect of the invention to improve the ease of adjusting the length of the rod. Furthermore, a simple method of length adjustment and dynamization for each strut is desired.

Based on the prior art, it is therefore an aspect of the invention to provide a telescopic strut, which can be readily and quickly changed in its length.

It is another aspect of the invention, to allow, as an alternative, fine adjustments of the struts.

In view of the above mentioned aspect it is furthermore another aspect of the invention to allow a quick switch between the two functions, i.e., to allow a quick first definition of the length of the telescopic element, and additionally, to switch for a fine adjustment of said length.

It is yet another aspect to provide a variable dynamization function to the strut which allows micro-motion at a fracture/fusion site to promote healing.

A telescopic strut of the present invention for use with an external fixator includes an axially extending rod having a series of circumferential grooves on an outer surface of the rod; an axially extending tube is provided for receiving the rod. The tube has a first end including a plurality of holes formed in a wall of the tube and a second end having a pin extending therethrough. A plurality of balls are provided for extending through the holes in the first end of the tube. A sleeve having an eccentric bore therethrough is mounted around the tube first end for contacting the balls. The eccentric bore has a major diameter allowing the balls to be located outside the grooves of the rod and a minor diameter causing the balls to be held within the grooves on the rod. A coupling element comprising a hollow tubular member is slidably mounted on an outer surface of the tube second end, the coupling element tubular member has two axially extending diametrically opposed slots for receiving the pin and an adjustment element is mounted on an outer surface of the coupling element tubular member for movement thereon in the axial direction. The adjustment member serves as a stop to limit the travel of the pin in the two slots. The adjustment member may be threaded and mounted on a mating thread on the coupling element tubular member.

A detent may be provided for holding the sleeve in a first position where the major diameter engages the balls or a second position where the minor diameter engages the balls. The means includes a spring biasing the sleeve towards the second position.

The grooves in the rod may be formed by a helical thread extending along the axial extent thereof so that rotation of the rod with the balls engaged lengthens the strut.

Alternately the grooves may be formed by a plurality of radial ridges.

Preferably the balls are at least partially retained within the holes of the leading end when contacted by the minor diameter of the sleeve.

A telescopic strut of the present invention for use with an external fixator may also comprise an axially extending rod, an axially extending tube moveably receiving the rod for varying the length of the rod and tube combination along a longitudinal axis. The tube has first and second ends, the second end having a pin extending therethrough. An adjustment system is mounted on the tube first end for adjusting the position of the rod in the tube. A connector element is provided having a tubular sleeve with a threaded outer surface mounted on an outer surface of the second end of the tube. The connector element can include a ball joint which can be locked when the connector is fixed in a hole in a ring of an external fixation frame. The sleeve has two axially extending diametrically opposed slots for receiving the pin and an adjustment element threadably mounted on a threaded portion of the tubular sleeve outer surface for axial movement along the axis. The adjustment element has an annular surface contacting the pin to limit the movement of the pin in the slots.

The rod is threaded and is mounted in the end of the tube such that relative rotation therebetween causes a length variation of the rod and tube combination along the longitudinal axis.

The adjustment system may include radially moveable elements which selectively engage and disengage the threaded rod to allow axial sliding when disengaged and fine adjustment by the relative rotation of the tube and rod when engaged to vary the strut length.

The tubular sleeve is coupled to an opening in an external fixation ring by releasable connectors which allow rotation of the sleeve and tube about the axis of the rod and tube to vary the axial length of rod and tube when the radially moveable elements are engaged.

The two slots in the connector sleeve each have a first end and the adjustment element can move the pin into contact with the slot first end to prevent the pin from moving in the two slots. The sleeve outer surface includes markings showing the distance between the slot first end and the pin wherein the markings are in 1 mm increments.

The pin may include a pair of protruding ends for receiving a tool for rotating the tubular sleeve and tube relative to the rod for varying the length of the strut.

An additional telescoping strut of the present invention for an external fixator comprises a threaded rod, a tube threadably receiving the rod with the tube and rod extending along a longitudinal axis. The tube has a first end with a pin extending therethrough. An adjustment element is provided for fixing the relative axial position of the tube and rod; and a dynamization system mounted on the first end of the tube, the system comprising a sleeve slidably mounted on the tube with the pin extending through a pair of diametrically opposed slots on the sleeve such that the pin can move in the axial direction with respect to the slots; an adjustable stop element mounted on the sleeve movable to limit the level of the pin in the slots. The adjustable stop element is a nut mounted on a threaded outer surface of the sleeve.

BRIEF DESCRIPTION OF THE DRAWINGS

The invention is now described with reference to the enclosed drawings, showing preferred embodiments of the telescopic strut:

FIG. 9 shows an adjustment wrench for adjusting the dynamization of the strut of the present invention;

FIG. 10 shows the same adjustment wrench adjusting the length of the strut of the present invention; and FIG. 11 is an isometric view of the wrench shown in FIGS. 9 and 10.

DETAILED DESCRIPTION

Figure 1:
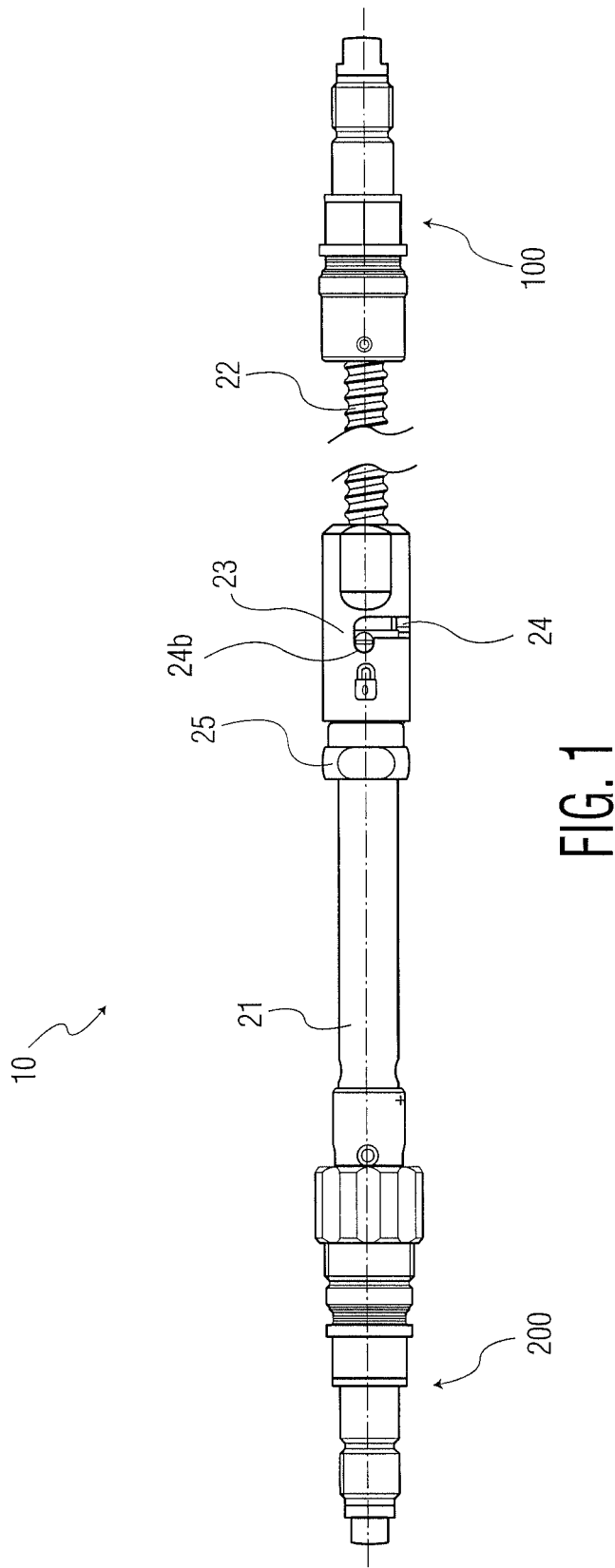
FIG. 1 is an elevation view of a telescopic strut according to the invention.

Referring to FIG. 1 there is shown a perspective view of a telescopic strut according to the invention generally denoted as 10. The telescopic strut comprises two free ends 11 and 12, which include coupling elements 100 and 200 being attachment points for connecting the strut to two external rings to be placed around the limb to be treated. The attachment coupling elements 100 and 200 according to this embodiment preferably comprise ball joints as will be discussed below, but this entirely depends on the kind of fixation element for which the rod is used.

Figure 2:
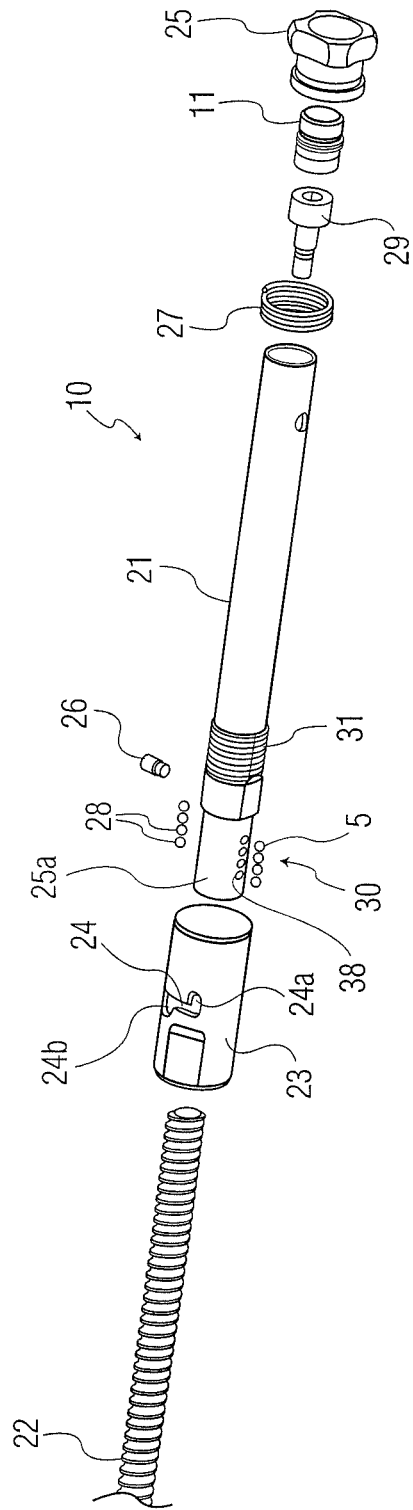
FIG. 2 is an exploded view of the length adjusting portion of the telescopic strut according to FIG. 1.

FIG. 1 shows the main components of the telescopic strut. There is an outer tube tubular element 21 having a bore in which the threaded rod 22 is partially located. Tube 21 has a bore therein for receiving rod 22 the bore can be only partially through tubular element 21 leaving a solid end adjacent coupling 200. The outer tube 21 has mating thread elements 30 for engaging threaded rod 222 which is located within a sleeve 23 at an end of tubular element 21 and are better seen in FIG. 2 as well as FIG. 3 and will be described below. In the preferred embodiment sleeve 23 comprises a bayonet groove 24 for a quick change between the desired quick length change mode and the fine adjustment mode. The sleeve 23 can be switched between two rotational positions for this, i.e., to lock and unlock movement the axial direction. Therefore the groove 24 has a U-form, the ends of the groove 24 defining the two positions with the help of a bolt 26 provided within the groove 24. The recessed ends 24a and 24b of the groove 24 are oriented in axial direction of the telescopic strut. These ends face in the same direction, towards the spring 27, as can be seen in FIG. 1 and the exploded view of FIG. 2, to allow displacement of the bolt 26 against the force of spring 27.

A security mechanism, to avoid unintentional switching, is realized by an additional nut 25, blocking the bolt 26 in one of the free ends of groove 24.

Figure 3:
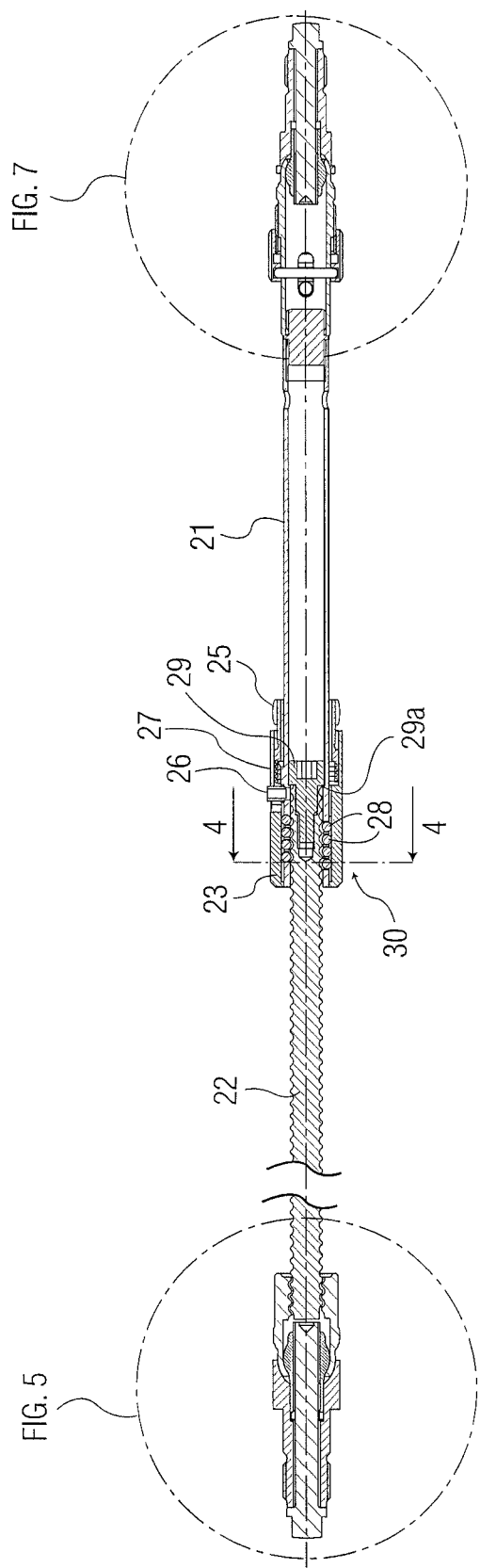
FIG. 3 is a side view in cross-section of the telescopic strut according to FIG. 1.

FIG. 3 shows a view in cross-section of the telescopic strut according to FIG. 1. Sleeve 23 can be pushed against action of spring 27 provided on the outer tube 21 and which spring is biased with help of nut 25. Then the sleeve 23 is turned around 90° and is arrested within the other free end 24a or 24b of the groove 24. It is preferred that this position is fixed through nut 25.

The turning angle of 90 degrees is defined in view of the way the quick length adjustment mode is working. This can be seen in FIG. 4 being a representation of a cross section of the rod along line 4-4 in FIG. 3. It can be seen from FIG. 4 that the sleeve 23 has a non-cylindrical inner bore. The bore can be, e.g., elliptical. The shorter diameter of the bore is sufficient to accommodate the outer diameter of the foremost portion 25a of outer tube 21 shown in FIG. 2, which is cylindrical. Foremost portion 25a comprises on both sides a plurality of preferably, four holes 38 to accommodate one ball 28 each. Of course, it is also possible to provide only two balls on each side or five or more. Three or four balls have been proven to be sufficient without lengthening the sleeve 23 too much.

Figure 4:
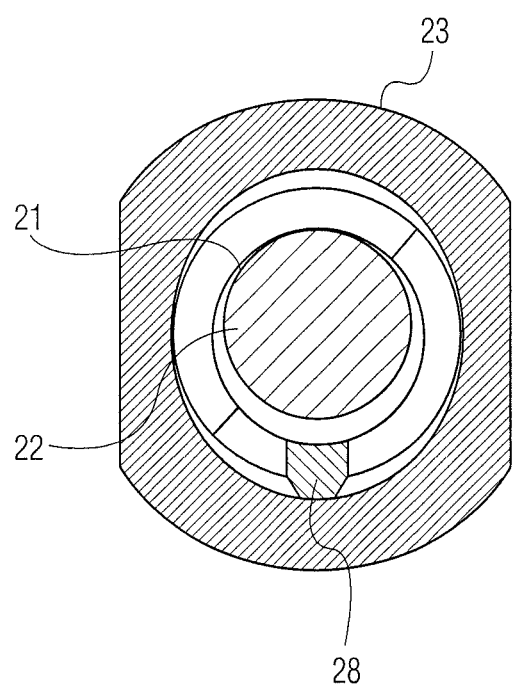
FIG. 4 is a cross section of the rod along line-4 in FIG. 3.

The inner diameter of outer tube 21 is greater than the outer thread portion of the rod 22 which is cylindrical. Therefore, the rod 22 can be pushed into the outer tube 21, when the bolt 26 is in a position which allows the sleeve 32 to be oriented as shown in FIG. 4. Then the balls 28 can freely move against the inner wall of sleeve 23 and the rod 22 can be axially pushed. For that the sum of the outer diameter of the rod 22 and twice the diameter of the balls 28 is less or nearly equal to the inner diameter of the sleeve 23.

Separation of the threaded rod 22 from the outer tube is prevented through an abutment screw 29 which is screwed into a corresponding thread within the threaded rod 22 and which can abut on a corresponding shoulder within the tube 21 as shown in FIG. 3

By turning the sleeve 23 around the bolt 26, i.e., by 90°, the balls 28 will be moved because of the elliptic inner shape within the sleeve 23. In this way the balls 28 are pushed through holes 38 towards the grooves of the thread 22 for interlocking, i.e., connecting the thread with the outer tube 21, because the balls 28 stand within both parts and leave no room to allow a direct axial movement of the threaded rod 22.

In this position the threaded rod 22 still can be moved axially through rotational movement of tube 21 being directly coupled via bolt 26 to sleeve 23 against the threaded rod 22 which can rotate in view of the balls 28 pressed in its threads. This allows for the fine adjustment.

Thus the elements allow for a quick change between free axial adjustment of the telescopic strut, if the balls 28 do not engage the threaded rod 22. If the balls do engage rod 22 then a fine adjustment through rotation of the outer tube 21/rod 22 is allowed. The balls 28 are engaging the one or subsequent grooves of the threaded rod 22, e.g., depending on the pitch of thread of the rod 22. The pitch angle of the thread can be chosen, e.g., between 30 and 60 degrees and especially between 40 and 50 degrees.

It is clear that this fine adjustment is only possible, if at least one free end 11 or 12 of the telescopic strut can be rotated while fixed within an external fixator ring.

Within another embodiment (not shown) a helically threaded rod is replaced by a rod having a plurality of radial grooves. Each of these grooves has dimensions to accommodate one of the balls 28. In other words, the threaded rod having a groove providing a pitch is replaced by a sequence of separated adjacent radial grooves. It is thus possible to use such a rod with a flank lead to block the device in a plurality of positions. However, with radial grooves it is not possible to allow a fine tuning through rotation of tube 21.

Figure 5:
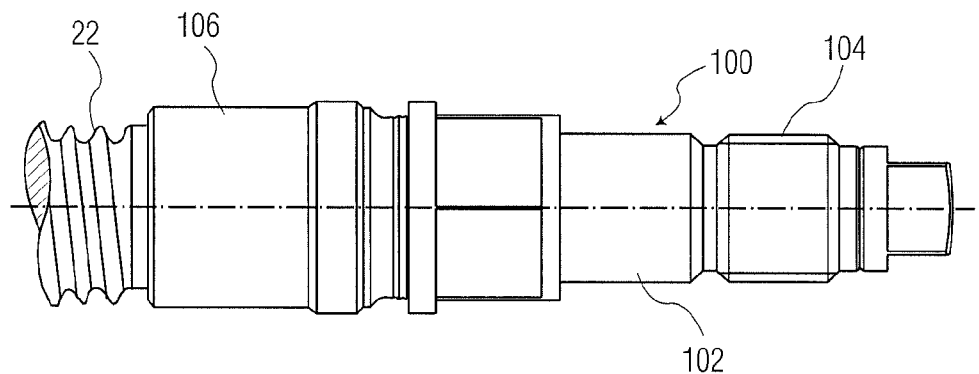
FIG. 5 is an elevation view of the coupling element connected to the threaded rod of the strut for coupling the strut to a ring of an external fixation system.
Figure 6:
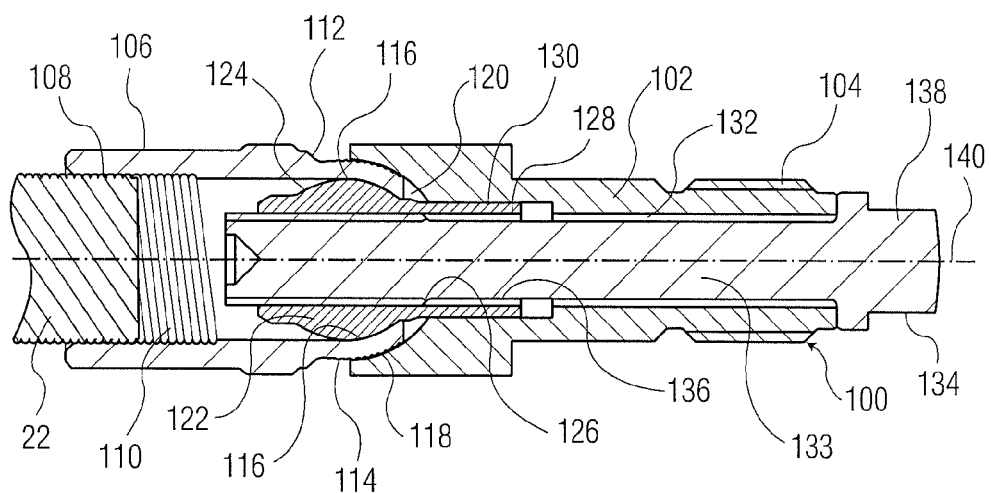
FIG. 6 is a cross-sectional view of the connector of FIG. 5.

Referring to FIGS. 5 and 6, there is shown a first coupling element adapted to engage a bore in a ring of an external fixation system. Typically the rings of an external fixation system are circular or part circular and have a plurality of through holes located between inner and outer diameters of the rings. FIGS. 5 and 6 show first coupling element 100, including a shaft 102 with a threaded portion 104 and a pivoting tubular end portion 106 adapted to thread on an end of rod 22 of strut 10. As can be seen in cross-sectional view FIG. 6, the inner bore 108 of end 106 includes threads 110 adapted to be screwed onto the end of rod 22. Pivot end 106 includes an end portion 112 having an outer part-spherical surface 114 and an inner part spherical surface 116. Outer part-spherical surface 114 may include roughened areas or ridges 118 so that it may be locked against a part spherical recess 120 on shaft portion 102 when the assembly is tightened. Pivot portion 106 is coupled to shaft portion 102 via a threaded nut 122 having a part spherical surface 124 adapted to engage inner part spherical surface 116 of pivot end 106. Nut 122 includes a threaded inner bore diameter 126. Nut 122 also includes a generally cylindrical leading end 128, which slidably engages a bore 130 within shaft 102. Shaft 102 includes a further bore portion 132 for receiving a screw 134, which bore has a smaller diameter than bore portion 130 so that leading end 128 of nut portion 122 may slidably engage the larger diameter bore 130 and still receive a threaded shaft 133 of a screw or tightening element 134 mounted in bore portion 132. Bore portions 130, 132 and shaft 133 extend along an axis 140. Screw element 134 may be threaded into the threaded bore 126 of nut 122 via an outer threaded portion 136 thereon. Tightening element 134 includes a drive head 138, which may be square or hexagonal so that a tool may be applied to rotate element 134 thereby moving surface 124 of nut 122 into tight engagement with inner surface 116 of pivot end 106. Portion 112 of pivot element 106 may have two or more longitudinal slits therein so that it may flex outwardly into engagement with part-spherical surface 120 upon movement of nut 122 toward surface 116 resulting from rotation of threaded tightening element or screw 134.

In use threaded portion 104 of coupling 100 is inserted through a hole in the external fixation system ring (not shown) and a nut is threaded onto thread 104 of shaft 102 to attach coupling element 100 to the ring. When this is done axis 140 of end 102 is co-axial with a central axis of the bore in the ring. When the end of rod 22 is threaded into pivot end 106, it can be selectively locked in position or rotated about the ball joint in any direction about axis 140 of coupling 100 on part-spherical surfaces 114 and 120 depending on whether screw element 134 and nut 122 are either in a loosened position or a tightened down position. When tightened roughened surface 118 engages inner surface 116 which ensures no movement of rod 22 with respect to the axis 140 of the hole in the ring and of portion 102.

Figure 7:
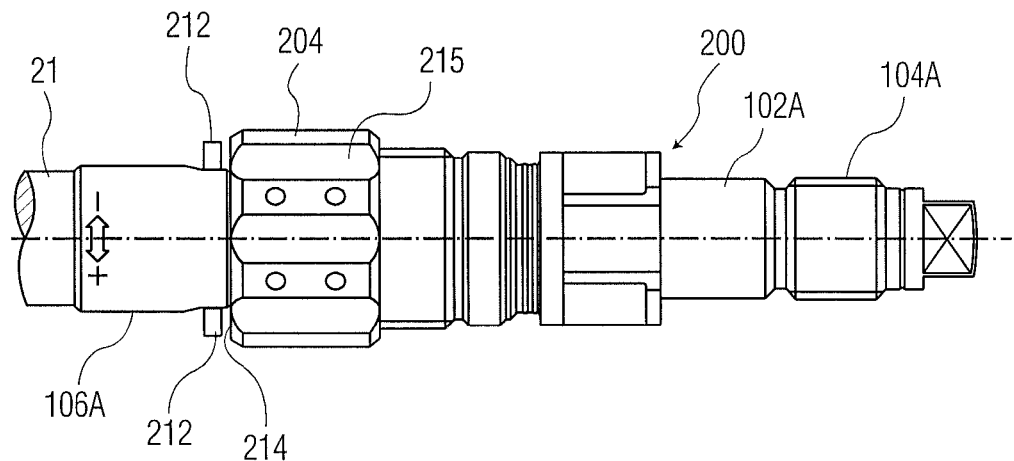
FIG. 7 is an elevation view of a coupling element connected to the tubular portion of the strut of the present invention for connecting the strut to a second ring element of an external fixation system.
Figure 8:
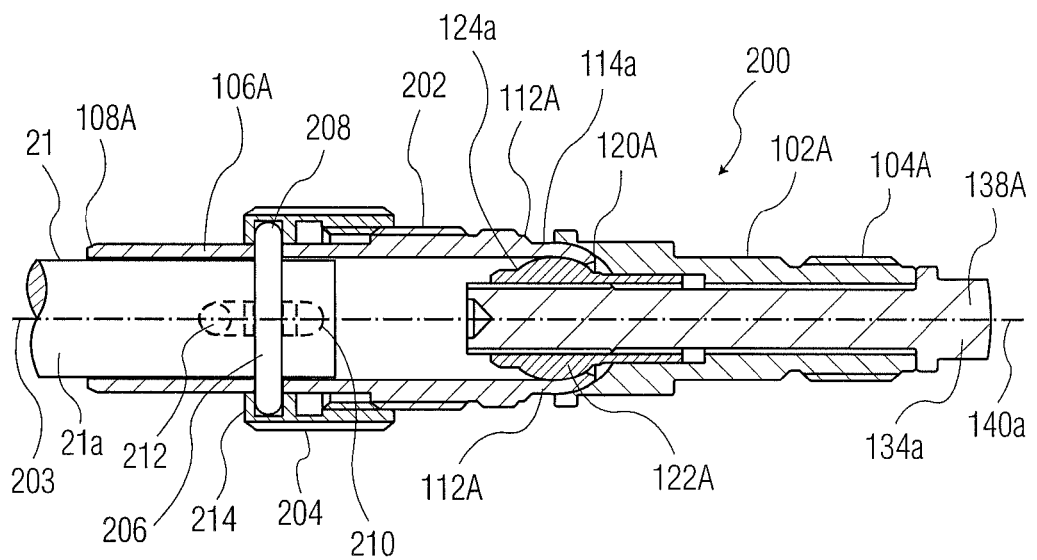
FIG. 8 is a cross-sectional view of the connection element of FIG. 7.

Referring to FIGS. 7 and 8, a second coupling element 200 is shown. Coupling element 200 includes many of the features of coupling 100, including a shaft 102a with a threaded portion 104a. Likewise, a screw 134a with drive head 138a is coupled to a nut 122a having the part spherical outer surface 124a. Also likewise, the coupling element 200 includes a pivoting tubular end portion 106a extending along an axis 203, which has a leading end 112a with part spherical surface 114a for contacting an inner surface 120a of element 102a. Tubular end 106a is slidably mounted on end 21a of shaft 21. End portion 106a includes a hollow end portion 108a fixedly receiving shaft 21 or an extension thereof such that pivot end portion 106a and shaft 21 cannot rotate relative to one another. Portion 106a now includes a threaded outer portion 202 upon which a rotatable internally threaded nut 204 is mounted. Rotation of nut 204 on threaded portion 202 moves the nut 204 along axis 203 either away from or toward end 108a and shaft 21. An O-ring 206 is mounted in a groove 208 within nut 204 to hold nut 204 in a particular axial location upon rotation of nut 204 on threaded portion 202. Tubular element 106a further includes a pair of slots 210 diametrically opposite one another in a wall of tubular element 106a. Shaft portion 21 includes a pin 212 extending therethrough which pin 212 is fixed to the end of shaft 21 such as by a press fit. Upon assembly, pin 212 extends through both slots 210 in 106a and extends outwardly beyond the outer surface on each side of tubular member 106a, a distance preferably approximately equal to the diameter of nut 204. Since tubular end portion 106a is slidable on end 21a of shaft 21 the engagement of slot 210 and pin 212 hold the tubular end portion 106a on end 21a. As will be discussed below, the engagement of end surface 214 of nut 204 with pin 212 as it moves within slot 210, provides for dynamization within the strut 10 by allowing the surgeon to set a dynamization distance of, for example, 0 mm to 5 mm by rotation of nut 204. This distance would be set by rotating nut 204 on thread 202. Typically, 1 mm spaced markings placed on the outer surface of tubular element 106a would indicate the distance.

In use, the telescopic strut would be used as described above and in U.S. Pat. No. 8,057,474, the teachings of which are hereby incorporated by reference, with the exception of the dynamization system discussed above. The surgeon connects strut with coupling elements 100 and 200 to respective first and second external fixation frame members such as rings or plates with the threadable elements 134, 134a loosened so that the part-spherical ball joints are free to rotate. The surgeon adjusts the length of the strut initially using the quick length adjustment mode and then the fine adjustment mode until the fractured bones are in the desired alignment. At this point, the screws 134, 134a are both tightened thereby locking the strut in the desired angular and length position with respect to both the first and second ring members. A further finer adjustment is needed then one of the ball joints must be loosened by rotating a screw 134a which allows for rotating the tubular shaft 21 or rod 22. Preferably the ball joint 200 is loosened by rotating screw 134a. The surgeon then sets the dynamization system by rotating nut 204. If no dynamization is required surface 214 of nut 204 is placed against pin 212. Obviously multiple struts 10 may be used in the frame system.

Referring to FIGS. 9-11, there is shown the use of a wrench 300 used to both make the fine adjustments of the length of strut 10, as well as set the dynamization distance between pin 212 and surface 214 of nut 204. Wrench 300 includes a first end 302 with a curved opening 304 defining first lobe 306, second lobe 308, and third lobe 310 adapted to respectively engage one of a plurality of grooves 215 on the outside of nut 204. As seen in FIG. 9, lobes 306, 308, and 310 engage three different grooves 215. Thus rotation of wrench 300 can move nut 204 on thread 202 either toward or away from pin 212. Tubular member 106a includes a series of markings 217 either cut or etched into the outer surface of tubular element 106a at 1 mm increments. Thus, the surgeon can set the dynamization by turning nut 204 thereby moving surface 214 with respect to pin 212. Preferably markings 217 are spaced 1 mm so that the exact amount of dynamization can be determined by counting the number of markings 217 between surface 214 and the under surface of pin 212.

Wrench 300 has a second end 320 with a pair of hook shaped elements 322 and 324, which each include a U-shaped recessed opening 326, which receives the ends of pin 212 which extend beyond the outer surface of tubular element 106s. As shown in FIG. 10, when end 320 is hooked over both ends of pin 212, wrench 320 can be used to rotate shaft 21. End 21a is slidably mounted within tubular element 106a however rotation of end 21a via pin 212 rotates tubular portion 106a via the engagement of pin 212 and slot 210 thus providing fine tuning of the length of strut 10. As discussed above, in order to accomplish this, the ball joint within coupling element 200 must be released by appropriately turning screw 134a. Once the correct length is achieved, the ball joint is again locked via rotation of screw 134a. Locking end 112a of sleeve 106a against surface 120a via threaded element 134a prevents rotation of shaft 21 about any axis Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system for adjusting the orientation of a pair of spaced rings or an external fracture fixator, comprising;
   an axially extending rod, a tubular element extending along a first axis for receiving the rod, the tubular element having a first end and a second end having a pin extending therethrough along a second axis perpendicular to the first axis of the tubular element and fixed to the tubular element second end, the pin having first and second end portions extending beyond an outer surface of the tubular element;
   a coupling element having a tubular member defining opposite side walls slidably mounted on an outer surface of the tubular element second end, the coupling element tubular member opposite side walls having two diametrically opposed elongated axially extending slots for receiving the pin at the tubular element second end and an adjustment element mounted on an outer surface of the coupling element tubular member for movement in the axial direction thereon, the adjustment element having a drive element formed on an outer surface to enable rotation of the adjustment element and having a surface for contacting the end portions of the pin serving as a stop to limit the travel of the pin in the elongated axially extending slots; and
   a wrench having first and second hook portions for engaging the first and second end portions of the pin and an opening for engaging the drive element on the adjustment element.

2. The system as set forth in claim 1 wherein the opening in the wrench has a plurality of lobes and the drive element of the adjustment element is a plurality of grooves formed on the outer surface of the adjustment element for receiving the plurality of lobes.

3. The system as set forth in claim 2 wherein the wrench opening has three lobes and the adjustment element outer surface has three grooves receiving the three lobes whereby rotation of the wrench about the first axis with the lobes engaging the ajustment element grooves causes the adjustment element to rotate.

4. The system as set forth in claim 1 wherein the wrench opening is located on a first end of the wrench and the first and second hook portions are located on a second end of the wrench.

5. The system as set forth in claim 1 wherein the wrench opening is concavely curved and has a shape corresponding to the drive element on the outer surface of the adjustment element for rotatably driving the adjustment element.

6. The system as set forth in claim 5 wherein the outer surface of the adjustment element has a plurality of axially extending grooves and the concave opening of the wrench has a plurality of lobes for the engaging grooves in the outer surface of the adjustment element.

7. A system for adjusting the orientation of a first and second ring element of an external fracture fixation system, comprising:
   an axially extending rod;
   an axially extending tube having a bore for receiving the rod, the rod moveable in the bore for varying a length of the rod and tube combination along a longitudinal axis;
   the axially extending tube having first and second ends, the second end having a pin extending therethrough, the pin fixed to the axially extending tube and having first and second end portions extending beyond an outer surface of the second end of the axially extending tube;
   a coupling element slidably mounted on the second end of the axially extending tube having a tubular element with a threaded outer surface mounted on the outer surface of the second end of the axially extending tube, the tubular element having two diametrically opposed elongated axially extending slots respectively receiving the first and second end portions of the pin in the tube second end and a dynamization element threadably mounted on the tubular element threaded outer surface for axial movement along the axis, the dynamization element having a surface contacting the pin first and second end portions to limit the movement of the pin in the slots;
   a wrench having first and second hook portions for engaging the first and second end portions of the pin and a concave opening for receiving the dynamization element.

8. The system as set forth in claim 7 wherein the two slots each have a first end and the dynamization element can move the pin into contact with the slot first end to prevent the pin from moving in the two slots.

9. The system as set forth in claim 8 wherein the couping element outer surface includes markings showing the distance between the slot first end and the pin.

10. The system as set forth in claim 9 wherein the markings are in 1 mm increments.

11. The system as set forth in claim 7 wherein the dynamization element includes a drive element for receiving the concave opening of the wrench for rotating the tubular element and tube relative to the rod for varying a length of the combined rod and tube.

12. The system as set forth in claim 11 wherein the opening in the wrench has a plurality of lobes and the drive element of the dynamization element has a plurality of grooves formed on the surface of the dynamization element for receiving the plurality of lobes.

13. The system as set forth in claim 12 wherein the wrench opening has three lobes and the dynamization element surface has three grooves receiving the three lobes whereby rotation of the wrench with the lobes engaging the dynamization element grooves causes the dynamization element to rotate about the longitudinal axis.

14. The system as set forth in claim 11 wherein the wrench opening is concavely curved and has a shape corresponding to the drive element on the outer surface of the dynamization element for rotatably driving the dynamization element.

15. The system as set forth in claim 14 wherein the outer surface of the dynamization element has a plurality of axially extending grooves and the concave opening of the wrench has a plurality of lobes for the engaging the grooves in the outer surface of the dynamization element.

16. The system as set forth in claim 7 wherein the wrench opening is located on a first end of the wrench and the first and second hook portions are located on a second end of the wrench.

17. A system for adjusting the orientation of a pair of spaced rings or an external fracture fixator, comprising:
a threaded rod;
a tubular member threadably receiving the rod, the tubular member and rod extending along a first axis, the tubular member having a first end with a pin extending therethrough, the pin fixedly mounted on the tubular member and having first and second end portions extending beyond an outer surface of the tubular member;
a dynamization system mounted on the first end of the tubular member, the dynamization system comprising a second sleeve slidably mounted on the tubular member with the pin fixed to the tubular member extending along a second axis transverse to the first axis through a pair of diametrically opposed slots on the second sleeve such that the pin can move in the first axis direction with respect to the slots and an adjustable stop element mounted on the second sleeve and having a circumferential surface for contacting the first and second end portions of the pin, the adjustable stop element movable to limit a level of the pin in the slots; and
a wrench having first and second hook portions for engaging the first and second end portions of the pin and an opening for engaging drive elements on the adjustable stop element.

18. The system as set forth in claim 17 wherein the opening in the wrench has a plurality of lobes and the drive elements of the adjustable stop element has a plurality of grooves formed on an outer surface of the adjustable stop element for receiving the plurality of lobes.

19. The system as set forth in claim 18 wherein the wrench opening has three lobes and the adjustable stop element outer surface has three grooves receiving the three lobes whereby rotation of the wrench with the lobes engaging the adjustable stop element grooves causes the adjustable stop element to rotate about the first axis.

* * * * *